United States Patent
Feldman et al.

(10) Patent No.: US 11,452,724 B2
(45) Date of Patent: Sep. 27, 2022

(54) METHODS FOR TREATING AMYOTROPHIC LATERAL SCLEROSIS

(71) Applicant: The Regents of the University of Michigan, Ann Arbor, MI (US)

(72) Inventors: Eva L. Feldman, Ann Arbor, MI (US); Ben Murdock, Ann Arbor, MI (US); Stephen Goutman, Ann Arbor, MI (US); Stacey Jacoby, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 231 days.

(21) Appl. No.: 16/855,623

(22) Filed: Apr. 22, 2020

(65) Prior Publication Data

US 2020/0253977 A1    Aug. 13, 2020

Related U.S. Application Data

(62) Division of application No. 16/539,289, filed on Aug. 13, 2019, now Pat. No. 10,660,895.

(60) Provisional application No. 62/718,122, filed on Aug. 13, 2018.

(51) Int. Cl.
| | |
|---|---|
| *C07D 487/04* | (2006.01) |
| *A61K 31/519* | (2006.01) |
| *A61P 25/00* | (2006.01) |
| *A61K 9/00* | (2006.01) |
| *A61K 31/428* | (2006.01) |
| *A61K 31/53* | (2006.01) |
| *A61K 31/7105* | (2006.01) |
| *A61K 31/4439* | (2006.01) |
| *A61K 31/444* | (2006.01) |
| *A61K 31/51* | (2006.01) |
| *A61K 31/4152* | (2006.01) |
| *A61K 31/133* | (2006.01) |

(52) U.S. Cl.
CPC ............ *A61K 31/519* (2013.01); *A61P 25/00* (2018.01); *A61K 9/0019* (2013.01); *A61K 31/133* (2013.01); *A61K 31/4152* (2013.01); *A61K 31/428* (2013.01); *A61K 31/444* (2013.01); *A61K 31/4439* (2013.01); *A61K 31/51* (2013.01); *A61K 31/53* (2013.01); *A61K 31/7105* (2013.01)

(58) Field of Classification Search
CPC .. C07D 487/04; C07D 471/04; C07D 413/12; C07D 413/14; C07D 403/12; C07D 403/14; C07D 471/14; C07D 418/22
See application file for complete search history.

(56) References Cited

U.S. PATENT DOCUMENTS

| | | |
|---|---|---|
| 2012/0328615 A1 | 12/2012 | Romagne et al. |
| 2015/0157597 A1 | 7/2015 | Tan et al. |
| 2017/0181993 A1 | 6/2017 | Hoffman |
| 2018/0000771 A1 | 1/2018 | Inoue et al. |

FOREIGN PATENT DOCUMENTS

| | | |
|---|---|---|
| CA | 3105117 | 1/2020 |
| EP | 2791141 | 10/2014 |
| WO | 2013/090490 | 6/2013 |
| WO | WO 2015/154012 | 10/2015 |
| WO | 2017/059224 | 4/2017 |

OTHER PUBLICATIONS

Allavena, P., et al., IL-15 is chemotactic for natural killer cells and stimulates their adhesion to vascular endothelium. J Leukoc Biol. Jun. 1997;61(6):729-35.
Allavena, P., et al., Regulation of adhesion and transendothelial migration of natural killer cells. Nat Immun. 1996-1997;15(2-3):107-16.
Beers, D. R., et al., CD4+ T cells support glial neuroprotection, slow disease progression, and modify glial morphology in an animal model of inherited ALS. Proc Natl Acad Sci U S A. Oct. 7, 2008; 105(40):15558-63.
Butovsky, O, et al., Modulating inflammatory monocytes with a unique microRNA gene signature ameliorates murine ALS. J Clin Invest. Sep. 2012;122(9):3063-87.
Changelian, P.S., et al., Prevention of organ allograft rejection by a specific Janus kinase 3 inhibitor. Science. Oct. 31, 2003;302(5646):875-8.
Chiu, IM, et al., T lymphocytes potentiate endogenous neuroprotective inflammation in a mouse model of ALS. Proc Natl Acad Sci U S A. Nov. 18, 2008; 105(46):17913-8.
Choi, S.S., et al., Interleukin-15 enhances cytotoxicity, receptor expression, and expansion of neonatal natural killer cells in long-term culture. Clin Diagn Lab Immunol. Sep. 2004;11(5):879-88.
Cudkowicz, et al., Trial of celecoxib in amyotrophic lateral sclerosis. Ann Neurol. Jul. 2006;60(1):22-31.
Fehniger, T.A., et al., Differential cytokine and chemokine gene expression by human NK cells following activation with IL-18 or IL-15 in combination with IL-12: implications for the innate immune response. J Immunol. Apr. 15, 1999; 162(8):4511-20.
Ferlazzo, G., et al., Distinct roles of IL-12 and IL-15 in human natural killer cell activation by dendritic cells from secondary lymphoid organs. Proc Natl Acad Sci U S A. Nov. 23, 2004;101(47):16606-11.
Finkelstein, A, et al., Abnormal changes in NKT cells, the IGF-1 axis, and liver pathology in an animal model of ALS. PLoS One. 2011;6(8):e22374.

(Continued)

*Primary Examiner* — Jeffrey H Murray
(74) *Attorney, Agent, or Firm* — Casimir Jones, SC; Robert A. Goetz

(57) ABSTRACT

Provided herein are methods for treating, delaying progression of, or reducing the severity of amyotrophic lateral sclerosis (ALS) in a subject through administration of therapeutically effective amounts of agents (e.g., JAK kinase inhibitors (e.g., tofacitinib)) capable of interfering with central nervous system related natural killer cell (NK) levels and function.

7 Claims, 5 Drawing Sheets

(56) References Cited

OTHER PUBLICATIONS

Flanagan, M.E., et al., Discovery of CP-690,550: a potent and selective Janus kinase (JAK) inhibitor for the treatment of autoimmune diseases and organ transplant rejection. J Med Chem. Dec. 23, 2010;53(24):8468-84.
Gordon, PH, et al., Efficacy of minocycline in patients with amyotrophic lateral sclerosis: a phase III randomised trial. Lancet Neurol. Dec. 2007;6(12):1045-53. Epub Nov. 5, 2007.
Hodge, J. A. et al. The mechanism of action of tofacitinib—an oral Janus kinase inhibitor for the treatment of rheumatoid arthritis. Clin Exp Rheumatol. Mar.-Apr. 2016;34(2):318-28.
Hooten, KG, et al, Protective and Toxic Neuroinflammation in Amyotrophic Lateral Sclerosis. Neurotherapeutics. Apr. 2015; 12(2):364-75.
Lanier, L.L., et al., Subpopulations of human natural killer cells defined by expression of the Leu-7 (HNK-1) and Leu-11 (NK-15) antigens. J Immunol. Oct. 1983; 131(4):1789-96.
Meininger, V, et al, Glatiramer acetate has no impact on disease progression in ALS at 40 mg/day: a double-blind, randomized, multicentre, placebo-controlled trial. Amyotroph Lateral Scler. Oct.-Dec. 2009; 10(5-6):378-83.
Meininger, V, et al., Pentoxifylline in ALS: a double-blind, randomized, multicenter, placebo-controlled trial. Neurology. Jan. 10, 2006;66(1):88-92.
Mitchell, JD, et al., Amyotrophic lateral sclerosis. Lancet. Jun. 16, 2007;369(9578):2031-2041.
Murdock, BJ, et al., The dual roles of immunity in ALS: injury overrides protection. Neurobiol Dis. May 2015;77:1-12.
Murdock, B. J. et al. Correlation of Peripheral Immunity With Rapid Amyotrophic Lateral Sclerosis Progression. JAMA Neurol. Dec. 1, 2017;74(12):1446-1454.
Rentzos, M., et al., Interleukin-15 and interleukin-12 are elevated in serum and cerebrospinal fluid of patients with amyotrophic lateral sclerosis. Eur Neurol. 2010;63(5):285-90.
Rode, M., et al., Perforin and Fas act together in the induction of apoptosis, and both are critical in the clearance of lymphocytic choriomeningitis virus infection. J Virol. Nov. 2004;78(22):12395-405.
Shimaoka, H., et al., A cytokine signal inhibitor for rheumatoid arthritis enhances cancer metastasis via depletion of NK cells in an experimental lung metastasis mouse model of colon cancer. Oncol Lett. Sep. 2017; 14(3):3019-3027.
Shresta, S., et al., Natural killer and lymphokine-activated killer cells require granzyme B for the rapid induction of apoptosis in susceptible target cells. Proc Natl Acad Sci USA. Jun. 6, 1995;92(12):5679-83.
Song, et al., Major histocompatibility complex class I molecules protect motor neurons from astrocyte-induced toxicity in amyotrophic lateral sclerosis. Nat Med. Apr. 2016;22(4):397-403.
Strowig, T., et al., Human NK cells of mice with reconstituted human immune system components require preactivation to acquire functional competence. Blood. Nov. 18, 2010;116(20):4158-67.
Van Gurp, E. et al. Phase 1 dose-escalation study of CP-690 550 in stable renal allograft recipients: preliminary findings of safety, tolerability, effects on lymphocyte subsets and pharmacokinetics. Am J Transplant. Aug. 2008;8(8):1711-8.
Van Vollenhoven, R., et al., Evaluation of the Short- Mid-, and Long-Term Effects of Tofacitinib on Lymphocytes in Patients With Rheumatoid Arthritis. Arthritis Rheumatol. May 2019;71(5):685-695.
Vivier, E., et al., Functions of natural killer cells. Nat Immunol. May 2008;9(5):503-10.
Zhao, W, et al., Immune-mediated mechanisms in the pathoprogression of amyotrophic lateral sclerosis. J Neuroimmune Pharmacol. Sep. 2013;8(4):888-99.
International Search Report and Written Opinion, International Patent Application No. PCT/US2019/046310, dated Oct. 29, 2019, 8 pages.
Morello Giovanna et al. "Selection and Prioritization of Candidate Drug Targets for Amyotrophic Lateral Sclerosis Through a Meta-Analysis Approach" Journal of Molecular Neuroscience, Cambridge, MA, vol. 61, No. 4, Feb. 24, 2017, pp. 563-580.
Supplementary EP Search Report, EP Patent Application No. 19849759.6, dated Apr. 22, 2022, 3 pages.

FIG. 1A
FIG. 1B
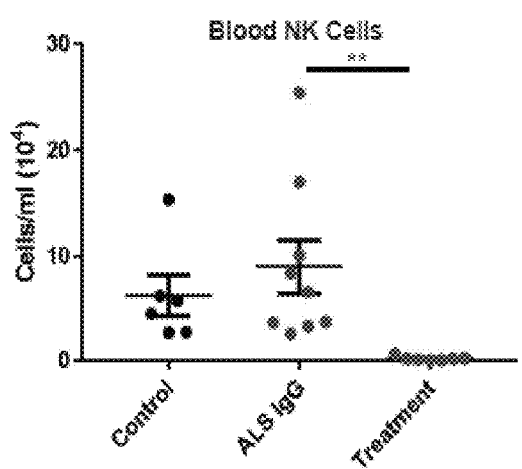
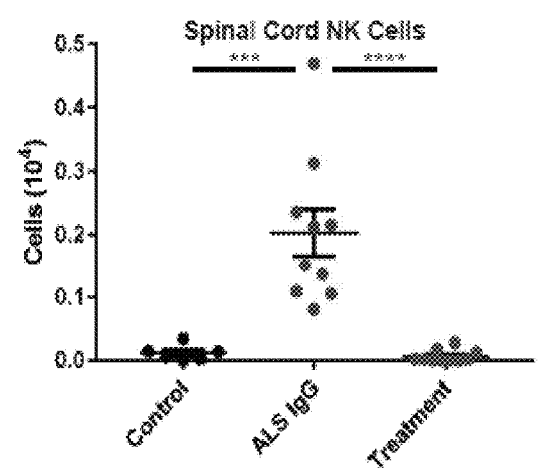

FIG. 2A
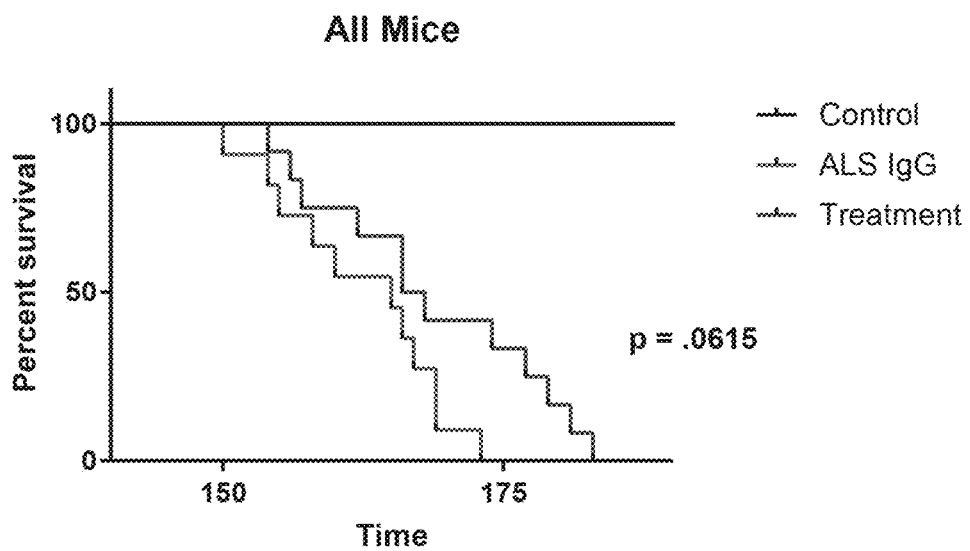
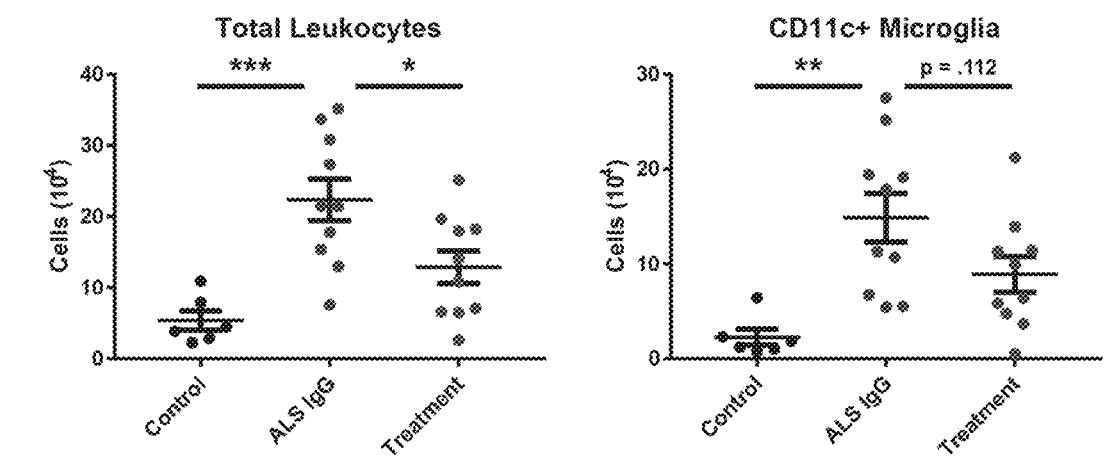
FIG. 2B    FIG. 2C

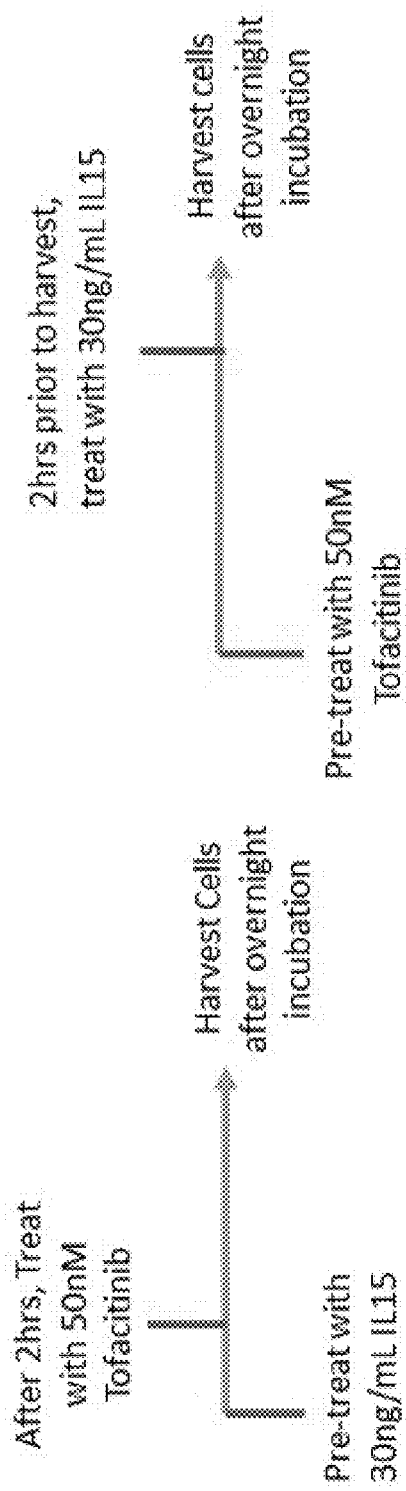
FIG. 3A
FIG. 3B
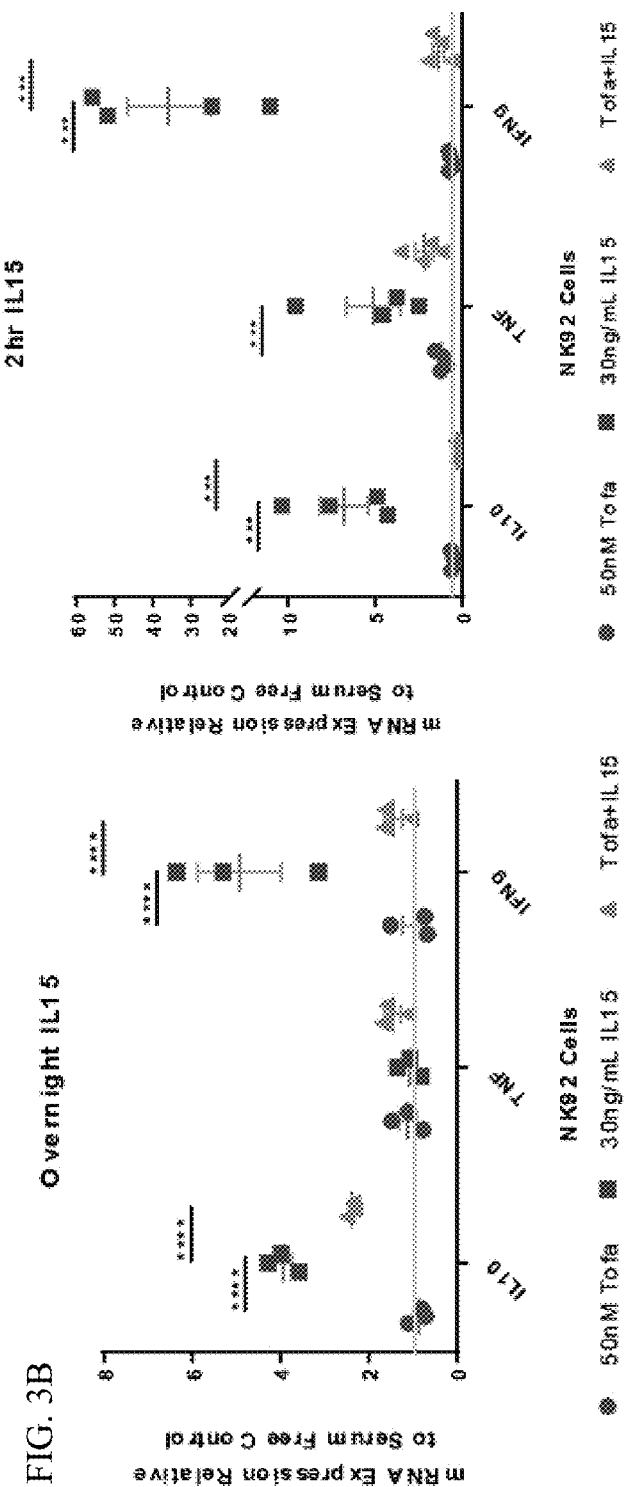

METHODS FOR TREATING AMYOTROPHIC LATERAL SCLEROSIS

The present application is a continuation of U.S. application Ser. No. 16/539,289, filed Aug. 13, 2019, which claims priority to U.S. Provisional application Ser. No. 62/718,122, filed Aug. 13, 2018, which are herein incorporated by reference in their entireties.

FIELD OF THE INVENTION

Provided herein are methods for treating, delaying progression of, or reducing the severity of amyotrophic lateral sclerosis (ALS) in a subject through administration of therapeutically effective amounts of agents (e.g., JAK kinase inhibitors (e.g., tofacitinib)) capable of interfering with central nervous system related natural killer cell (NK) levels and function.

INTRODUCTION

Amyotrophic lateral sclerosis (ALS) is a devastating, adult-onset illness characterized by motor neuron degeneration at all levels of the motor system. Depending on the site of onset, initial symptoms include dysarthria, dysphagia, and proximal or distal weakness. Disease progression involves muscle atrophy, spasticity, hyperreflexia, paralysis, and eventually respiratory failure (see, Mitchell J D, Borasio G D, Lancet 2007, 369:2031-41). With a prevalence of 3.9 per 100,000 in the US, the expected lifespan following diagnosis is 3-5 years (see, Mehta P, Antao V, Kaye W, Sanchez M, Williamson D, Bryan L, Muravov O, Horton K, Division of T, Human Health Sciences AfTS, Disease Registry AG, Centers for Disease C, Prevention: Prevalence of amyotrophic lateral sclerosis—United States, 2010-2011. Morbidity and mortality weekly report Surveillance summaries 2014, 63 Suppl 7:1-14). There is no cure, and treatment options are limited. Studies demonstrate that the immune system plays a key role in ALS progression (see, Murdock B J, et al., Neurobiology of disease 2015, 77:1-12; Hooten K G, et al., Neurotherapeutics: the journal of the American Society for Experimental NeuroTherapeutics 2015, 12:364-75; Zhao W, et al., Journal of neuroimmune pharmacology: the official journal of the Society on NeuroImmune Pharmacology 2013, 8:888-99); however, the role of the immune system is unclear, as various aspects can play both a beneficial and detrimental role in the disease course. Attempts to universally suppress the immune system in ALS patients have had at best a negligible effect on progression or at worst have accelerated the disease (see, Cudkowicz M E, et al., Annals of neurology 2006, 60:22-31; Meininger V, et al, Amyotrophic lateral sclerosis: official publication of the World Federation of Neurology Research Group on Motor Neuron Diseases 2009, 10:378-83; Meininger V, et al., Neurology 2006, 66:88-92; Gordon P H, et al., The Lancet Neurology 2007, 6:1045-53). Alternatively, augmenting or depleting specific immune cell populations in ALS mouse models alters the disease course and can slow disease progression (see, e.g., Chiu I M, et al., Proceedings of the National Academy of Sciences of the United States of America 2008, 105:17913-8; Butovsky O, et al., The Journal of clinical investigation 2012, 122:3063-87; Finkelstein A, et al., PloS one 2011, 6:e22374). Thus, there is a critical need to identify immune cell populations to serve as therapeutic targets.

The present invention addresses this need.

SUMMARY OF THE INVENTION

Natural killer (NK) cells are immune cells that play a key role in combating cancer and infection (see, Vivier, E., et al., Nature immunology 9, 503-510, doi:10.1038/ni1582 (2008)). These cells patrol the tissue and eliminate other cells that are infected or have become cancerous. In addition, they are responsible for eliminating sick or dying cells. Normally cells in the body are protected from NK cell-mediated cytotoxicity via expression of major histocompatibility complex class I (MHC I). However, motor neurons in ALS lack MHC I expression in both human patients and mouse models (see, Song et al., Nature medicine 22, 397-403, doi:10.1038/nm.4052 (2016)) making them incredibly vulnerable to NK cells. Increased NK cell levels can also be detected in the central nervous system (CNS) of ALS mice (see, Finkelstein, A. et al. PloS one 6, e22374, doi:10.1371/journal.pone.0022374 (2011)) and the periphery of ALS patients (see, Murdock, B. J. et al. JAMA neurology, doi: 10.1001/jamaneurol.2017.2255 (2017)).

Experiments conducted during the course of developing embodiments for the present invention determined that NK cells contribute to ALS progression thereby indicating the targeting NK cells as a viable therapeutic option. Moreover, experiments conducted during the course of developing embodiments for the present invention determined that tofacitinib was able to hinder and/or inhibit NK cell maintenance, expansion and cytotoxicity against other cells through one or more of hindering and/or inhibiting IL-15 signaling, hindering and/or inhibiting IL-10 expression, hindering and/or inhibiting IFN-γ expression, reducing perforin levels, and hindering and/or inhibiting NK cell migration.

Tofacitinib inhibits the janus kinase (JAK) pathway that is crucial for polarization of immune cells and production of pro-inflammatory cytokines. Rather than suppressing the immune system as a whole, tofacitinib prevents the immune system from skewing towards a destructive phenotype. In addition, expression of cytokines which regulate NK cell levels and activity are reduced by tofacitinib (see, Hodge, J. A. et al. Clinical and experimental rheumatology 34, 318-328 (2016)), and NK cell levels are reduced in a dose dependent manner (see, Hodge, J. A. et al. Clinical and experimental rheumatology 34, 318-328 (2016); van Gurp, E. et al. American journal of transplantation: official journal of the American Society of Transplantation and the American Society of Transplant Surgeons 8, 1711-1718, doi: 10.1111/j.1600-6143.2008.02307.x (2008)) while maintaining CD4 T cell levels (see, van Gurp, E. et al. American journal of transplantation: official journal of the American Society of Transplantation and the American Society of Transplant Surgeons 8, 1711-1718, doi:10.1111/j.1600-6143.2008.02307.x (2008)) which have been shown to be protective in ALS (see, Murdock, B. J. et al. JAMA neurology, doi:10.1001/jamaneurol.2017.2255 (2017); Beers, D. R., et al., Proceedings of the National Academy of Sciences of the United States of America 105, 15558-15563, doi: 10.1073/pnas.0807419105 (2008)).

Accordingly, the present invention provides methods of treating, delaying progression of, or reducing the severity of amyotrophic lateral sclerosis (ALS) in a subject, the method comprising administering to a subject in need thereof a therapeutically effective amount of an agent (e.g., JAK kinase inhibitors (e.g., tofacitinib)), wherein the therapeutically effective amount is sufficient to interfere with central nervous system related natural killer cell (NK) levels and function.

In some embodiments, the administering of the agent is specifically targeted to the central nervous system of the subject. In some embodiments, the administering of the agent is specifically targeted to ALS motor neurons. In some embodiments, the administering of the agent is specifically targeted to ALS motor neurons having reduced levels of MHC-1 in comparison with normal levels of MHC-1. In some embodiments, the administering of the agent is specifically targeted to spinal cord cells.

In some embodiments, the subject is a mammalian subject (e.g., mouse, horse, human, cat, dog, gorilla, chimpanzee, etc.). In some embodiments, the subject is a human patient suffering from or at risk of suffering from ALS.

In some embodiments, the administering results in hindering and/or inhibiting NK cell maintenance, expansion and cytotoxicity against motor neuron cells through one or more of hindering and/or inhibiting IL-15 signaling, hindering and/or inhibiting IL-10 expression, hindering and/or inhibiting IFN-γ expression, reducing perforin levels, and hindering and/or inhibiting NK cell migration.

The present invention contemplates that interfering with central nervous system related natural killer NK levels and function satisfies an unmet need for the treatment of ALS as such treatment results in reduced CNS inflammation, and/or prevention of motor neuron vulnerability to NK cell activity. Moreover, such treatment does not affect CD4 T cell levels.

Such methods are not limited to administering of specific agents. In some embodiments, the agents are selected from AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), and XL019. In some embodiments, the agents are JAK kinase inhibitors. For example, in some embodiments, such agents are capable of inhibiting JAK1, JAK2 and/or JAK3. In some embodiments, the agents are JAK3 inhibitors.

In some embodiments, the therapeutically effective amount is an amount sufficient to detectably reduce or ameliorate one or more symptoms of the ALS. In some embodiments, the one or more symptoms comprise difficulty lifting the front part of the foot; difficulty lifting the toes; weakness in one or both legs; weakness in one or both feet; weakness in one or both ankles; hand weakness; hand clumsiness; slurring of speech; trouble swallowing; muscle cramps; twitching in one or both arms; twitching in one or both shoulders and/or twitching of the tongue.

In some embodiments, the agent is formulated to be administered locally. In some embodiments, the agent is formulated to be administered systemically, intravenously, intraarterially, subcutaneously, or intrathecally.

In certain embodiments of the invention, combination treatment with the agent and a course of a drug known for treating ALS (e.g., one or more of riluzole, ceftriaxone, dexpramipexole, creatine+tamoxifen, rasagiline, pioglitazone, arimoclomol, pyrimethamine, trantinoin+pioglitazone, edaravone, and an antisense molecule or interfering RNA directed against an RNA encoding superoxide dismutase) are provided for ALS treatment. Since the doses for all approved drugs known for treating ALS are known, the present invention contemplates the various combinations of them with the previously described agents.

In certain embodiments, the agent is administered for purposes of reducing CNS related inflammation.

In certain embodiments, the agent is administered for purposes of preventing motor neuron vulnerability related to NK cell exposure.

The invention also provides pharmaceutical compositions comprising the agent in a pharmaceutically acceptable carrier.

The invention also provides kits comprising one or more agents (e.g., agents sufficient to interfere with central nervous system related NK levels and function) and instructions for administering the agent to an animal. The kits may optionally contain one or more other therapeutic agents, e.g., riluzole, ceftriaxone, dexpramipexole, creatine+tamoxifen, rasagiline, pioglitazone, arimoclomol, pyrimethamine, trantinoin+pioglitazone, edaravone, and an antisense molecule or interfering RNA directed against an RNA encoding superoxide dismutase.

BRIEF DESCRIPTION OF DRAWINGS

FIG. 1A-B: Flow cytometric analysis of NK cells (NK1.1+) in WT and ALS mice following NK cell depletion treatment. NK cell levels in the peripheral blood (A) and spinal cord (B) of control WT mice, ALS mice with mock treatment, and NK cell depletion treatment are shown. $p<0.01$, *$p<0.001$, ****$p<0.0001$.

FIG. 2A-C: Changes in survival and CNS inflammation following NK cell depletion treatment. (A) Survival of control WT mice, ALS mice with mock treatment, and NK cell depletion treatment are shown. Total leukocyte accumulation (B) and accumulation of CD11c+ microglia (C) in the CNS of control WT mice, ALS mice with mock treatment, and NK cell depletion treatment are shown. *$p<0.05$, $p<0.01$, *$p<0.001$.

FIG. 3A-E: Tofacitinib reduces NK cell activity and cytotoxicity. (A) NK cells (NK92 cell line) were treated with tofacitinib either after 30 ng/ml of IL-15 activation overnight (ON) or before IL-15 activation (2-hours) to test its efficacy in inhibiting already activated NK cells (overnight stimulation) or preventing their activation (2-hour stimulation). (B) NK cells cultured Overnight or 2 Hrs with IL-15 were lysed and cytokine expression assessed using qPCR. IL-10, TNF-α, and IFN-γ gene expression was assessed. (C) Intracellular granzyme B and perforin were levels were assessed in NK cells in vitro using flow cytometry. Fluorescent intensity was plotted for unstimulated NK cells in serum free conditions (negative control; blue), serum-stimulated NK cells (positive control; red), IL-15 stimulated NK cells (30 ng/ml IL-15; orange), or tofacitinib treated NK cells (30 ng/ml IL-15+ tofacitinib; green). (D) NK cell migration was assessed using a transwell assay. NK92 cells were fluorescently labeled and placed on one side of a well separated by a porous membrane. A chemoattractant (serum or CCL13) was placed on the other side of the transwell and after 3 hours the fluorescent intensity in the chemoattractant half of the well was assessed. (E) NK cytotoxicity was measured using a K562 co-culture assay. NK92 NK cells were cultured under multiple conditions and then co-cultured at a 4:1 ratio with K562 cancer cells overnight. Cells were then stained with a viability dye and analyzed using flow cytometry. Lower K562 survival indicates greater NK cell cytotoxicity.

DETAILED DESCRIPTION OF THE INVENTION

Figure 3C:
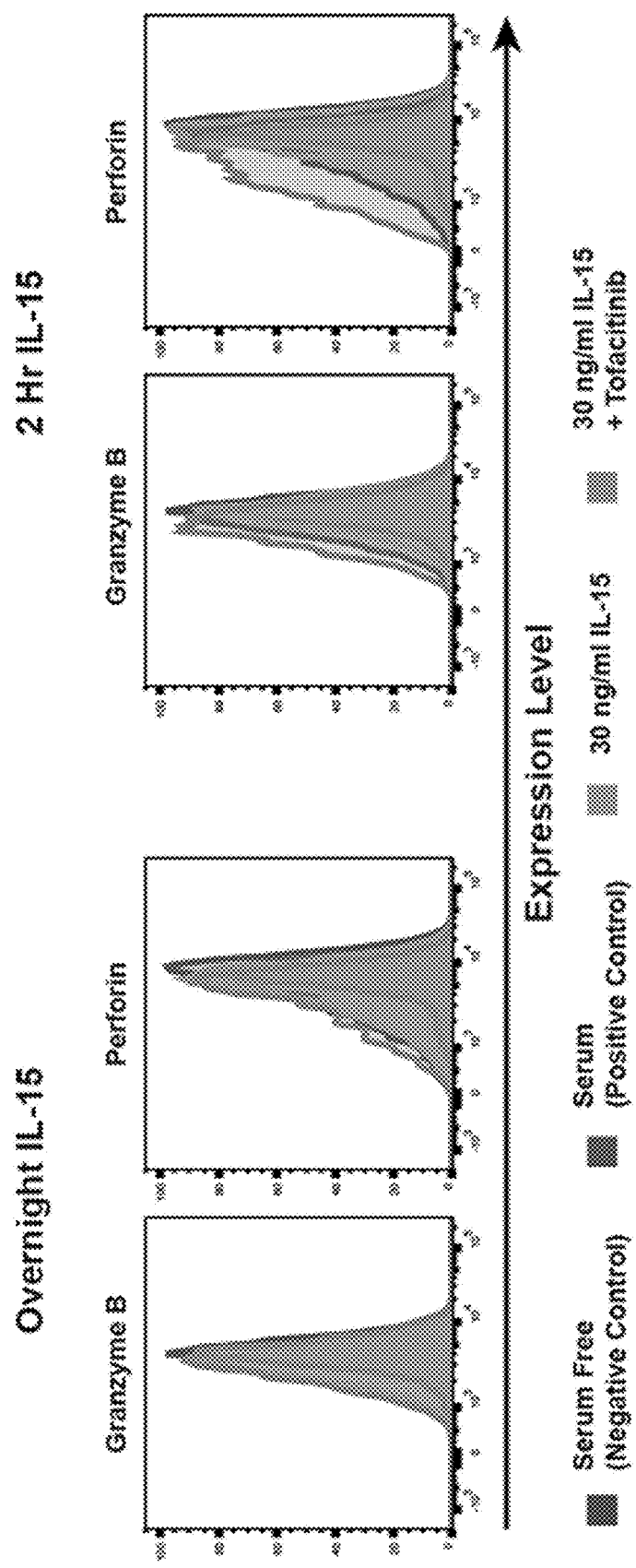

ALS, commonly referred to as Lou Gehrig's disease, is characterized by selective, premature degeneration and death of motor neurons in the motor cortex, brain stem and spinal cord. The loss of motor neurons causes progressive muscle paralysis ultimately leading to death from respiratory failure. Approximately 90% of all ALS cases are sporadic amyotrophic lateral sclerosis, without a family history of the disease, and the other approximately 10 percent of cases are cases of familial amyotrophic lateral sclerosis.

Neuroinflammation is a hallmark of ALS in both human patients and mouse models (see, Murdock B J, et al., Neurobiology of disease 2015, 77:1-12; Zhao W, et al., Journal of neuroimmune pharmacology: the official journal of the Society on NeuroImmune Pharmacology 2013, 8:888-99). While motor neuron degeneration underlies clinical symptoms, it is becoming increasingly clear that the immune system plays a key role in pathology. A variety of insults give rise to identical immune responses which produce the characteristic clinical and histopathological manifestations of motor neuron disease. This makes the immune system an attractive target for therapeutics, as the wide variety of potential ALS sources all funnel through a common immunological pathway over the course of disease (see, Hooten K G, et al, Neurotherapeutics: the journal of the American Society for Experimental NeuroTherapeutics 2015, 12:364-75). Despite previous studies implicating natural killer (NK) and natural killer T (NKT) cells in ALS, very little has been done to explore the role of these cells during ALS, as previous studies have focused on CD4 T cells, monocytes, or microglia (see, Murdock B J, et al., Neurobiology of disease 2015, 77:1-12; Zhao W, et al., Journal of neuroimmune pharmacology: the official journal of the Society on NeuroImmune Pharmacology 2013, 8:888-99). Thus, examination and modulation of NK and NKT cells in ALS is a highly attractive avenue of investigation.

Experiments conducted during the course of developing embodiments for the present invention determined that NK cells contribute to ALS progression thereby indicating the targeting NK cells as a viable therapeutic option. Moreover, experiments conducted during the course of developing embodiments for the present invention determined that tofacitinib was able to hinder and/or inhibit NK cell maintenance, expansion and cytotoxicity against motor neuron cells through one or more of hindering and/or inhibiting IL-15 signaling, hindering and/or inhibiting IL-10 expression, hindering and/or inhibiting IFN-γ expression, reducing perforin levels, and hindering and/or inhibiting NK cell migration.

Accordingly, the present invention provides methods of treating, delaying progression of, or reducing the severity of amyotrophic lateral sclerosis (ALS) in a subject, the method comprising administering to a subject in need thereof a therapeutically effective amount of an agent (e.g., JAK kinase inhibitors (e.g., tofacitinib)), wherein the therapeutically effective amount is sufficient to interfere with central nervous system related natural killer cell (NK) levels and function.

In some embodiments, the administering of the agent is specifically targeted to the central nervous system of the subject. In some embodiments, the administering of the agent is specifically targeted to ALS motor neurons. In some embodiments, the administering of the agent is specifically targeted to ALS motor neurons having reduced levels of MHC-1 in comparison with normal levels of MHC-1. In some embodiments, the administering of the agent is specifically targeted to spinal cord cells.

In some embodiments, the subject is a mammalian subject (e.g., mouse, horse, human, cat, dog, gorilla, chimpanzee, etc.). In some embodiments, the subject is a human patient suffering from or at risk of suffering from ALS.

In some embodiments, the administering results in hindering and/or inhibiting NK cell maintenance, expansion and cytotoxicity against motor neuron cells through one or more of hindering and/or inhibiting IL-15 signaling, hindering and/or inhibiting IL-10 expression, hindering and/or inhibiting IFN-γ expression, reducing perform levels, and hindering and/or inhibiting NK cell migration.

The present invention contemplates that interfering with central nervous system related natural killer NK levels and function satisfies an unmet need for the treatment of ALS as such treatment results in reduced CNS inflammation, and/or prevention of motor neuron vulnerability to NK cell activity. Moreover, such treatment does not affect CD4 T cell levels.

Such methods are not limited to administering of specific agents. In some embodiments, the agents are selected from AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), and XL019. In some embodiments, the agents are JAK kinase inhibitors. For example, in some embodiments, such agents are capable of inhibiting JAK1, JAK2 and/or JAK3. In some embodiments, the agents are JAK3 inhibitors.

In some embodiments, the therapeutically effective amount is an amount sufficient to detectably reduce or ameliorate one or more symptoms of the ALS. In some embodiments, the one or more symptoms comprise difficulty lifting the front part of the foot; difficulty lifting the toes; weakness in one or both legs; weakness in one or both feet; weakness in one or both ankles; hand weakness; hand clumsiness; slurring of speech; trouble swallowing; muscle cramps; twitching in one or both arms; twitching in one or both shoulders and/or twitching of the tongue.

In some embodiments, the agent is formulated to be administered locally. In some embodiments, the agent is formulated to be administered systemically, intravenously, intraarterially, subcutaneously, or intrathecally.

In certain embodiments of the invention, combination treatment with the agent and a course of a drug known for treating ALS (e.g., one or more of riluzole, ceftriaxone, dexpramipexole, creatine+tamoxifen, rasagiline, pioglitazone, arimoclomol, pyrimethamine, trantinoin+pioglitazone, edaravone, and an antisense molecule or interfering RNA directed against an RNA encoding superoxide dismutase) are provided for ALS treatment. Since the doses for all approved drugs known for treating ALS are known, the present invention contemplates the various combinations of them with the previously described agents.

Compositions within the scope of this invention include all compositions wherein the described agent (e.g., agents sufficient to interfere with central nervous system related NK levels and function) are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example demonstrates that NK cells contribute to ALS progression.

There is an important immune component to the progression of ALS. Indeed, the immune system is protective during early stages of the disease, but becomes destructive as disease progresses. As such, targeting specific immune populations can extend lifespan of ALS mice.

Experiments were conducted to test if NK cells contribute to ALS progression. It has been shown that NK cells kill infected, cancerous or dying cells, and are increased in ALS patient blood compared with healthy patients. NK cells have been shown to be increased in spinal cords of ALS mice. NK cells kill other cells that are missing MHC-1. As ALS related motor neuron cells lack MHC-1, the role of NK cells in ALS progression was investigated.

To test whether NK cells contribute to ALS progression, SOD1$^{G93A}$ ALS mice were treated with a weekly dose of NK cell depleting antibody and mouse survival and CNS inflammation assessed. The depleting antibody targets NK cells expressing the marker NK1.1; this marker is only present on half of NK cells in heterozygous SOD1$^{G93A}$ ALS mice but effectively eliminated all NK1.1$^+$ cells (or half of all NK cells) in the periphery (FIG. 1A). In addition, depletion eliminated accumulation of NK1.1$^+$ NK cells in the CNS (FIG. 1B). This 50% NK reduction in the periphery and CNS resulted in extended lifespan for ALS mice (FIG. 2A) and reduced total inflammation in the CNS (FIG. 2B) due to a reduced number of inflammatory microglia (FIG. 2C). Together, these data indicate that NK cells are contributing to ALS progression, and targeting NK cells a viable therapeutic option.

Example II

As noted, it has been found that NK cells accumulate in the central nervous system (CNS) of ALS mice (see, Chiu, I. M., et al., Proc Natl Acad Sci USA, 2008. 105(46): p. 17913-8; Finkelstein, A., et al., PLoS One, 2011. 6(8): p. e22374), that molecular signals that drive NK cell proliferation and activation are increased in the peripheral blood and CNS of ALS patients (see, Rentzos, M., et al., Eur Neurol, 2010. 63(5): p. 285-90), and that motor neurons in both ALS mice and human patients are more vulnerable to NK cell-mediated damage (see, Song, S., et al., Nat Med, 2016. 22(4): p. 397-403). The results presented in Example I indicate that depletion of NK cells can reduce neuroinflammation in ALS mice and increase survival. In addition, as ALS patients have increased NK cell levels during early stages of disease such results indicate a targeting of NK cells is an attractive ALS therapy. In addition, as tofacitinib is capable of reducing peripheral NK cells in mice (see, Shimaoka, H., et al., Oncol Lett, 2017. 14(3): p. 3019-3027) and human patients (see, van Vollenhoven, R., et al., Arthritis Rheumatol, 2019. 71(5): p. 685-695; van Gurp, E., et al., Am J Transplant, 2008. 8(8): p. 1711-8), such targeting of NK cells as an attractive ALS therapy can be accomplished through use of such a therapeutic (e.g., JAK kinase inhibitor (e.g., tofacitinib)).

Tofacitinib functions by blocking cytokine signaling via the JAK/STAT pathway (see, Changelian, P. S., et al., Science, 2003. 302(5646): p. 875-8; Flanagan, M. E., et al., J Med Chem, 2010. 53(24): p. 8468-84). One of the pathways blocked is the IL-15 signaling pathway which is crucial to maintaining and expanding NK cell populations (see, Strowig, T., et al., Blood, 2010. 116(20): p. 4158-67; Ferlazzo, G., et al., Proc Natl Acad Sci USA, 2004. 101(47): p. 16606-11). This likely explains the reduction in NK cell levels in patients being treated with tofacitinib (see, van Vollenhoven, R., et al., Arthritis Rheumatol, 2019. 71(5): p. 685-695; van Gurp, E., et al., Am J Transplant, 2008. 8(8): p. 1711-8). However, IL-15 also plays an important role in the activation and cytotoxicity of NK cells (see, Fehniger, T. A., et al., J Immunol, 1999. 162(8): p. 4511-20; Allavena, P., et al., Nat Immun, 1996. 15(2-3): p. 107-16; Allavena, P., et al., J Leukoc Biol, 1997. 61(6): p. 729-35; Choi, S. S., et al., Clin Diagn Lab Immunol, 2004. 11(5): p. 879-88). Thus, in addition to reducing overall NK cell levels, tofacitinib may suppress NK cell activity in ALS patients further reducing motor neuron damage.

To test this possibility, experiments were conducted that utilized the well-characterized NK92 NK cell line to assess tofacitinib's impact on NK cell activation and cytotoxicity in vitro. Two separate conditions were used (FIG. 3A): NK cells were pre-treated with IL-15 for 2 hours and then cultured overnight with tofacitinib (Overnight IL-15) to assess the ability of tofacitinib to suppress previously activated cells, or NK cells were treated overnight with tofacitinib and then stimulated with IL-15 for 2 hours to assess the ability of tofacitinib (2 Hr IL-15) to prevent future activation. First, NK cells from these two conditions were collected, lysed, and cytokine expression gene expression was assessed using qPCR (FIG. 3B). IL-10 and IFN-γ expression was significantly increased by overnight IL-15 treatment while IL-10, IFN-γ, and TNF-α (a first response inflammatory cytokine) were significantly increased following 2 hour IL-15 stimulation. In contrast, both IL-10 and IFN-γ expression were significantly reduced by tofacitinib treatment or pre-treatment.

Experiments were next conducted that examined the intracellular levels of granzyme B and perforin—two proteins used by NK cells to induce apoptosis in target cells (see, Shresta, S., et al., Proc Natl Acad Sci USA, 1995. 92(12): p. 5679-83; Rode, M., et al., J Virol, 2004. 78(22): p. 12395-405)—in NK cells using flow cytometry (FIG. 3C). NK cells were stimulated overnight with IL-15 or for two hours in the presence or absence of tofacitinib; unstimulated NK cells cultured in serum-free media were used as negative controls while NK cells cultured in serum were used as positive controls. Following culture, NK cells were permeabilized and stained intracellularly with fluorescently tagged antibodies for granzyme B and perforin. NK cells were then analyzed using flow cytometry to assess average NK cell granzyme B and perforin levels. While tofacitinib had a modest effect on granzyme B levels, perforin levels were reduced by tofacitinib treatment, particularly in NK cells that had been treated with tofacitinib prior to IL-15 stimulation.

Figure 3D:
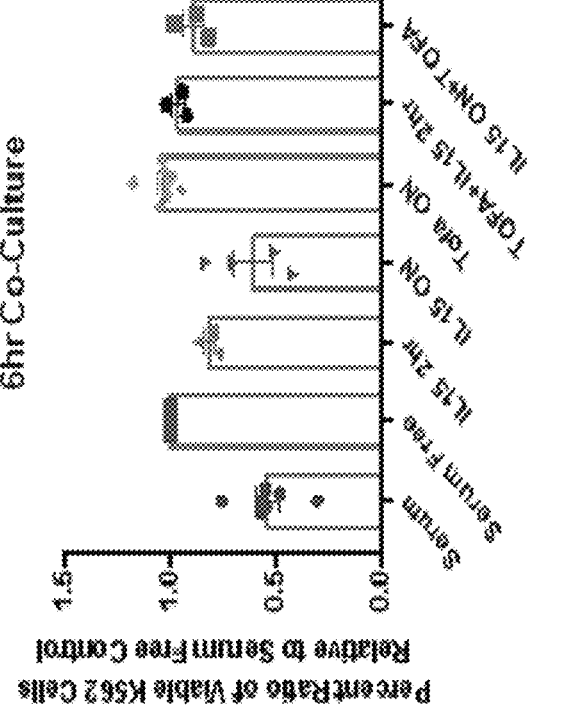
Figure 3E:
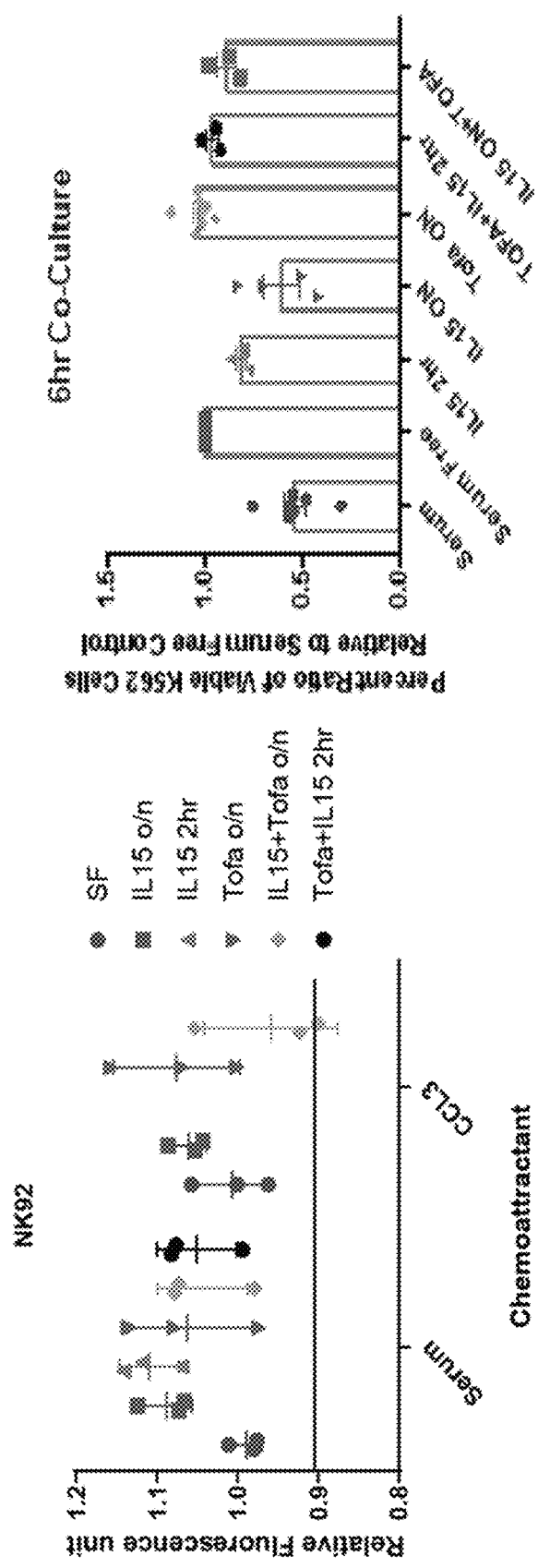

Experiments were conducted to assess the impact on NK cell migration following tofacitinib treatment (FIG. 3D). Using a commercially available kit, NK92 NK cells were placed in one half of a well bisected by a porous membrane. NK cell chemoattractants (serum or CCL13) were then placed in the other half of the well and the number of NK cells which traversed the membrane were measured. Cells stimulated with IL-15 with or without tofacitinib; NK cells cultured without serum were used as a negative control. The results indicate that tofacitinib treatment has a modest reduction on NK cell migration in response to serum as a chemoattractant and a more robust suppression of migration in response to CCL13. Finally, to assess whether tofacitinib can suppress NK cell-mediated killing, experiments were conducted that utilized a well-established co-culture model system whereby NK cells were cultured with K562 cancer cells and K562 survival was used to measure NK cytotoxicity (see, Lanier, L. L., et al., J Immunol, 1983. 131(4): p. 1789-96). NK cells were cultured under serum free conditions (negative control), with serum (positive control), with IL-15 for 2 hours, with IL-15 overnight, with tofacitinib alone, with IL-15 for 2 hours+tofacitinib, or with IL-15 overnight+tofacitinib (FIG. 3E). These NK cells were then co-cultured with K562 cancer cells at a 4:1 NK:K562 ratio overnight. Cells were collected, stained with a viability dye, and analyzed using flow cytometry. All data were normalized to NK cells cultured in the absence of serum (negative control) to account for run-to-run variation. It was found that NK cells cultured in serum were the most cytotoxic, with 50% of the K562 cells having been killed by NK cells. Increasing duration of IL-15 stimulation resulted in decreasing K562 viability (and therefore increasing NK cell cytotoxicity), with overnight stimulation resulting in cytotoxicity compared to serum-activated NK cells. In contrast, NK cell damage was ameliorated by tofacitinib treatment even following overnight IL-15 stimulation.

Experiments were next conducted that examined NK cell activation levels in a small group (n=10) of human age and gender-matched ALS and control patients. NK cells were isolated using a commercially available kit and expression of NK cell activation genes was measured using Nanostring. Increased expression of activation genes was observed in ALS patients (Table 1) and across multiple visits. These data indicate that NK cells in ALS patients are more activated than those in healthy control patients and that tofacitinib may be used to treat ALS.

TABLE 1

ALS NK cells have increased expression of activation genes at multiple visits throughout the disease course.

| Visit 1 | | Visit 3 | |
| --- | --- | --- | --- |
| Gene | Fold Increase | Gene | Fold Increase |
| TLR4 | 2.01007 | IFITM3 | 2.074841 |
| CD163 | 2.01876 | LGMN | 2.203973 |

TABLE 1-continued

ALS NK cells have increased expression of activation genes at multiple visits throughout the disease course.

| Visit 1 | | Visit 3 | |
| --- | --- | --- | --- |
| Gene | Fold Increase | Gene | Fold Increase |
| HDC | 2.076797 | CABLES1 | 2.208529 |
| CLEC7A | 2.213999 | CDC25A | 2.259465 |
| CEACAM3 | 2.264911 | CD109 | 2.33005 |
| IRF4 | 2.285483 | CD163 | 2.545128 |
| LGMN | 2.291829 | CCR5 | 2.612723 |
| TCL1A | 2.355277 | GRIA1 | 2.666322 |
| IL3RA | 2.45314 | MYCT1 | 3.336048 |
| CCR2 | 2.578101 | EGR1 | 3.521062 |
| EGR1 | 2.71921 | RBFOX3 | 3.596707 |
| SYP | 3.122873 | CD8B | 3.812471 |
| CD8B | 3.211431 | MS4A1 | 3.942064 |
| MS4A1 | 3.987846 | APOE | 4.882311 |
| IFITM3 | 5.238768 | SYP | 5.57167 |

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A kit comprising a therapeutically effective amount of an agent capable of interfering with central nervous system related natural killer cell (NK) levels and function and instructions for administering the agent to a subject having or at risk of having ALS, wherein the agent is a JAK kinase inhibitor, wherein the agent is selected from AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), and XL019.

2. The kit of claim 1, wherein the JAK kinase inhibitor is a JAK1 kinase inhibitor, a JAK2 kinase inhibitor, and/or a JAK3 kinase inhibitor.

3. The kit of claim 1, wherein the therapeutically effective amount is an amount sufficient to detectably reduce or ameliorate one or more symptoms of the ALS, wherein the one or more symptoms comprise difficulty lifting the front part of the foot; difficulty lifting the toes; weakness in one or both legs; weakness in one or both feet; weakness in one or both ankles; hand weakness; hand clumsiness; slurring of speech; trouble swallowing; muscle cramps; twitching in one or both arms; twitching in one or both shoulders and/or twitching of the tongue.

4. The kit of claim 1, wherein the subject is a human subject.

5. The kit of claim 4, wherein the subject is a human patient suffering from or at risk of suffering from ALS.

6. The kit of claim 1, wherein the agent is formulated to be administered systemically, intravenously, intraarterially, subcutaneously, or intrathecally.

7. The kit of claim 1, further comprising one or more of riluzole, ceftriaxone, dexpramipexole, creatine+tamoxifen, rasagiline, pioglitazone, arimoclomol, pyrimethamine, trantinoin+pioglitazone, edaravone, and an antisense molecule or interfering RNA directed against an RNA encoding superoxide dismutase.

\* \* \* \* \*